(12) United States Patent
Ikeda et al.

(10) Patent No.: US 8,580,532 B2
(45) Date of Patent: Nov. 12, 2013

(54) METHOD FOR STABILIZING α-THROMBIN IN THROMBIN-CONTAINING SOLUTION

(75) Inventors: Remi Ikeda, Ryugasaki (JP); Chizuru Morikawa, Ryugasaki (JP); Hirokazu Yago, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 852 days.

(21) Appl. No.: 12/519,191

(22) PCT Filed: Dec. 6, 2007

(86) PCT No.: PCT/JP2007/001367
§ 371 (c)(1),
(2), (4) Date: Jun. 15, 2009

(87) PCT Pub. No.: WO2008/075455
PCT Pub. Date: Jun. 26, 2008

(65) Prior Publication Data
US 2010/0047834 A1 Feb. 25, 2010

(30) Foreign Application Priority Data
Dec. 21, 2006 (JP) .................................. 2006-344121

(51) Int. Cl.
*A61K 38/43* (2006.01)
*A61K 9/19* (2006.01)

(52) U.S. Cl.
USPC .............................. 435/13; 435/214; 435/188

(58) Field of Classification Search
None
See application file for complete search history.

(56) References Cited

U.S. PATENT DOCUMENTS

| | | | |
|---|---|---|---|
| 4,696,812 A | 9/1987 | Silbering et al. | |
| 2001/0033837 A1 | 10/2001 | Metzner et al. | |
| 2006/0182735 A1 | 8/2006 | Metzner et al. | |
| 2008/0311104 A1* | 12/2008 | Senderoff et al. | 424/94.64 |
| 2009/0101809 A1* | 4/2009 | Wilbert | 250/281 |

FOREIGN PATENT DOCUMENTS

| | | |
|---|---|---|
| EP | 1 136 084 | 9/2001 |
| EP | 1 221 479 A1 | 7/2002 |
| JP | 62-106028 | 5/1987 |
| JP | 64-40433 | 2/1989 |
| JP | 2004-191367 | 7/2004 |

OTHER PUBLICATIONS

Landis et al. (1981) J. Biol. Chem. 256(9): 4604-10.*
Bauer et al. (1980) J. Biol. Chem 255(12): 5900-03.*
D. V. Brezniak, et al., "High stability of dilute human alpha-thrombin in salt solutions", Blood Coagulation and Fibrinolysis, vol. 5, No. 5, XP009129320, Jan. 1, 1994, pp. 847-848.
D. W. T. Nilsen, et al., "Binding of Various Thrombin Fractions to Fibrin and the Influence of AT-III on Their Adsorption", Thrombosis and Haemostasis, vol. 55, No. 3, XP009129338, Jun. 30, 1986, pp. 352-356.
Fenton, II J.W., "Human Thrombins Production, Evaluation, and Properties of Alpha-Thrombin", The Journal of Biological Chemistry, vol. 252, No. 11, pp. 3587-3598, (1977).
Karlsson, G., "Analysis of human alpha-thrombin by hydrophobic interaction high-performance liquid chromatography", Protein Expression and Purification, vol. 27, pp. 171-174, (2003).
Boissel, J.P., "Covalent Structures of Beta and Gamma Autolytic Derivatives of Human Alpha-Thrombin", The Journal of Biological Chemistry, vol. 259, No. 9 pp. 5691-5697, (1984).
Chang, J.Y. "The structures and proteolytic specificities of autolysed human thrombin", Biochem. J. vol. 240, pp. 797-802, (1986).

* cited by examiner

*Primary Examiner* — Lisa J Hobbs
(74) *Attorney, Agent, or Firm* — Oblon, Spivak, McClelland, Maier & Neustadt, L.L.P.

(57) ABSTRACT

To provide a method for stabilizing unstable α-thrombin in a thrombin-containing solution, a solution containing stabilized α-thrombin, and a liquid fibrinogen assay reagent containing the solution. The method for stabilizing α-thrombin in a thrombin-containing solution, which includes adjusting the percentage of α-thrombin to 70% or more with respect to the amount of total thrombin in the thrombin-containing solution.

14 Claims, 3 Drawing Sheets

A  ← α-Thrombin (human-derived)
Molecular weight 36,800

B  ← β, γ-Thrombin
Molecular weight 28,000

METHOD FOR STABILIZING α-THROMBIN IN THROMBIN-CONTAINING SOLUTION

CROSS-REFERENCE TO RELATED APPLICATIONS

This application is a National Stage of PCT/JP07/001367 filed Dec. 6, 2007 and claims the benefit of JP 2006-344121 filed Dec. 21, 2006.

TECHNICAL FIELD

The present invention relates to a method for stabilizing unstable α-thrombin contained in a thrombin-containing solution, to a thrombin-containing solution containing stabilized α-thrombin, and to a liquid fibrinogen assay reagent containing the solution.

BACKGROUND ART

Fibrinogen is a precursor of fibrin, which is a predominant protein that forms blood clots, and is produced in liver parenchyma cells. In the human body, about 80% of fibrinogen is present in plasma (e.g., about 200 to 400 mg/dL in a healthy adult), and the remaining amount is present in tissues. Fibrinogen is a glycoprotein containing three paired polypeptide (i.e., Aα, Bβ and γ) chains coupled via a disulfide bond. When the Aα chains and the Bβ chains are cleaved from fibrinogen by thrombin, fibrin is formed. Fibrin plays the main role in thrombus formation and hemostasis. Clinically, fibrinogen increases under the condition of inflammation, and decreases in severe hepatic disorders, DIC, etc.

Fibrinogen can be assayed through the Clauss method (thrombin addition method), the PT-derived method (clotting time method), TIA (tubidimetric immunoassay), the latex method, etc. Among them, the thrombin addition method is commonly employed. Specifically, thrombin and calcium chloride are added to a sodium citrate-added plasma sample, and the clotting time is measured. The fibrinogen concentration (mg/dL) in the sample is calculated by a calibration curve obtained from clotting times at known fibrinogen concentrations.

A thrombin employed in fibrinogen assay is α-thrombin, which is produced through cleavage of a peptide from prothrombin (i.e., precursor of thrombin) and exhibits a clotting activity. The α-thrombin is known to undergo self-decomposition to form β-thrombin, or further to form γ-thrombin, which are low molecular weight thrombins with no clotting activity. Therefore, α-thrombin is generally lyophilized for long-term storage.

Several attempts have been made to stabilize thrombin in a solution. For example, there have been known several methods such as: (1) a method in which high-concentration glycerol and polyol (e.g., sucrose, mannitol, sorbitol, etc.) are added to thrombin (Patent Document 1); and (2) a method in which saccharide, amino acid, etc. are added to thrombin (Patent Document 2).

However, these methods exhibit an unsatisfactory effect of stabilizing thrombin in a liquid fibrinogen assay reagent.

One known stabilization method for thrombin contained in a fibrinogen assay reagent includes adding a thrombin antagonist to a thrombin-containing solution (Patent Document 3).

However, the mechanism of this method is based on inhibition of the activity of thrombin. Therefore, when this method is employed, the clotting time of a low-fibrinogen-concentration sample, which is an important sample in fibrinogen assay, is considerably prolonged, and in some cases not detectable. Prolongation of the clotting time causes reduction in sample throughput and failure in assaying of low-fibrinogen-concentration samples causes an increase in the number of samples to be re-assayed. Thus, the above method is not suited for an emergency medical test.

Under such circumstances, there is demand for a method for stabilizing α-thrombin in an α-thrombin-containing solution which can be performed on low-fibrinogen-concentration samples without causing considerable prolongation of assay time and with little effects on measurements, thus being applicable to liquid fibrinogen assay reagents.

Patent Document 1: JP-A-1987-106028
Patent Document 2: JP-A-1989-040433
Patent Document 3: JP-A-2004-191367

DISCLOSURE OF THE INVENTION

Problems to be Solved by the Invention

An object of the present invention is to provide a method for stabilizing unstable α-thrombin present in a thrombin-containing solution, a solution containing stabilized α-thrombin, and a liquid fibrinogen assay reagent containing the solution.

Means for Solving the Problems

The present inventors have carried out extensive studies in order to attain the aforementioned objects, and have found that β-thrombin and γ-thrombin, which were previously considered to be merely self-decomposition products of α-thrombin, have stronger activity of decomposing α-thrombin than the self-decomposition activity of α-thrombin. Quite surprisingly, the inventors have also found that, through suppressing the amount(s) of β-thrombin and/or γ-thrombin with respect to the amount of total thrombin to fall within a certain low range, α-thrombin, which has been previously considered to be an unstable due to self-decomposition activity, can be stabilized in an α-thrombin-containing solution. The present invention has been accomplished on the basis of these findings.

Accordingly, the present invention provides a method for stabilizing α-thrombin in a thrombin-containing solution, which includes adjusting the percentage of α-thrombin to 70% or more with respect to the amount of total thrombin in the thrombin-containing solution.

Effects of the Invention

According to the present invention, decrease in percent remaining and activity of α-thrombin in a thrombin-containing solution can be prevented, whereby storage stability and quality of the thrombin-containing solution can be improved. Furthermore, the invention can improve storage stability and quality of a liquid fibrinogen assay reagent suitable for emergency medical tests.

BRIEF DESCRIPTION OF THE DRAWINGS

FIG. 1 10-20% SDS-PAGE images of purified thrombin. The left image corresponds to purified α-thrombin, and the right image corresponds a mixture of purified β- and γ-thrombins. A denotes a band attributed to α-thrombin, and B denotes a band attributed to β- and γ-thrombins.

BEST MODES FOR CARRYING OUT THE INVENTION

Figure 1:

In the present invention, the α-thrombin content with respect to the amount of total thrombin in a thrombin-containing solution is 70% or more, preferably 80% or more, more preferably 90% or more. Still more preferably, the α-thrombin content is 70% or more and the β- and/or γ-thrombin content is less than 30%, yet more preferably the α-thrombin content is 80% or more and the β- and/or γ-thrombin content is less than 20%, and particularly preferably the α-thrombin content is 90% or more and the β- and/or γ-thrombin content is less than 10%, with respect to the amount of total thrombin in a thrombin-containing solution.

In the present invention, as described in the Examples hereinbelow, as the β- and γ-thrombin content with respect to the amount of total thrombin increases, the increased β- and γ-thrombin reduces the percent remaining and activity of α-thrombin in a thrombin-containing solution. Therefore, through elevating the α-thrombin content with respect to the amount of total thrombin and, in turn, reducing the β- and γ-thrombin content with respect to the amount of total thrombin, storage stability and quality of α-thrombin in a solution can be improved.

As used herein, the term "thrombin" refers to thrombin including α-thrombin, and the term "total thrombin" refers to α-thrombin, β-thrombin and γ-thrombin.

In the present invention, the α-thrombin content with respect to the amount of total thrombin may be determined based on the following equation (1) upon measuring α-thrombin, β-thrombin and γ-thrombin, respectively through a known quantitative thrombin determination method.

$$\alpha\text{-Thrombin content (\%) with respect to the amount of total thrombin}=(\alpha\text{-thrombin/total thrombin})\times 100 \quad (1)$$

Similarly, the β- and/or γ-thrombin content with respect to the amount of total thrombin may be determined based on the following equation (2).

$$\beta\text{- and/or }\gamma\text{-Thrombin content (\%) with respect to the amount of total thrombin}=(\beta\text{- and/or }\gamma\text{-thrombin/total thrombin})\times 100 \quad (2)$$

Thrombin can be quantitated through, for example, activity measurement or protein determination by densitometry. Any methods may be employed. Before measurement, α-thrombin and decomposition products thereof may be optionally isolated or purified through any known methods.

More specifically, when the α-thrombin content is determined through the activity measurement method (a chromogenic substrate method) using a chromogenic substrate S-2238 (product of Daiichi Pure Chemicals Co., Ltd.), α-, β-, and γ-thrombins are fractionated by means of a known ion-exchange resin, and the decomposition activity of each fraction to S-2238 is determined, whereby the relative α-thrombin activity (%) to the total thrombin activity can be determined.

Also, when densitometry is employed, α-, β-, and γ-thrombins are fractionated through a known electrophoresis method for protein analysis, and the protein content of each fraction is determined through densitometry, whereby the protein content of α-thrombin (%) to the protein content of the total thrombins can be determined.

The thrombin species employed in the present invention may be any of thrombins derived from animal such as human, thrombins prepared by genetic engineering, and commercially available as pharmaceutical products.

The thrombins employed in the present invention may be prepared through known protein separation/purification procedures; e.g., filtration, washing, drying, recrystallization, chromatographic treatments, HPLC, and liquid-liquid-separation. More specifically, there may be employed ion-exchange resins such as cation-exchange resin; affinity resin such as benzamidine resin; ultrafiltration membrane; and gel filtration.

Combination of these procedures may be appropriately designed so that the α-thrombin content with respect to the amount of total thrombin can be increased.

The thrombin-containing solution of the present invention is an aqueous solution, an organic solvent solution, or a water-organic solvent mixed solution in which thrombin is suspended or dissolved in water and/or organic solvent. Among them, aqueous solution and water-organic solvent mixed solution are preferred. No particular limitation is imposed on the organic solvent, so long as it does not impair fibrinogen measurement (e.g., by decomposition or inhibiting activity of α-thrombin). Examples of the organic solvent include dimethyl sulfoxide, glycerol, polyethylene glycol, and polypropylene glycol. These solvents may be used singly or in combination of two or more species.

The pH of the thrombin-containing solution of the present invention is not necessarily controlled. However, the pH is preferably 4 to 9, more preferably 5.5 to 7, still more preferably 6 to 6.5, in order to prevent decomposition and inhibiting activity of α-thrombin.

For adjusting the pH to 4 to 9, a buffer which can control the pH to fall within a range of 4 to 9 may be appropriately employed. Examples of such a buffer include citric acid, phosphoric acid, acetic acid, imidazole, HEPES, MOPS, BIS-TRIS, TRIS, MOPSO, ADA, and MES. These buffers may be used singly or in combination of two or more species.

In the case where the pH is adjusted to 5.5 to 7, or to 6 to 6.5, citric acid, phosphoric acid, imidazole, BIS-TRIS, MOPSO, ADA, MES, etc. may be used. These buffers may be used singly or in combination of two or more species.

No particular limitation is imposed on the amount of buffer(s) added to the thrombin-containing solution, so long as buffering action can be ensured. For example, the buffer concentration of a thrombin-containing solution is preferably to 1000 mM, particularly preferably 20 to 300 mM.

No particular limitation is imposed on the α-thrombin activity of the thrombin-containing solution of the present invention, so long as the α-thrombin activity is adjusted to a target value depending on the α-thrombin content with respect to the amount of total thrombin. For example, when the thrombin-containing solution is employed as a fibrinogen assay reagent, the α-thrombin activity is preferably 20 to 1,000 units/mL as determined through a known chromogenic substrate method, more preferably 50 to 500 units/mL, particularly preferably 100 to 300 units/mL.

The thrombin-containing solution of the present invention may appropriately contain known compounds as mentioned below so long as the fibrinogen assay is not impeded, and may be prepared through a known production method.

The thrombin-containing solution may appropriately contain a known compound employed for, for example, stabilizing α-thrombin or improving storage stability of α-thrombin so long as the fibrinogen assay is not impeded. Examples of such compounds may include calcium ions, organic acids, surfactants, and proteins.

Specific examples of the calcium ions preferably include a water-soluble calcium compound, such as calcium chloride, calcium lactate, calcium gluconate, calcium glucuronate, and calcium tartrate. These calcium compounds may be used singly or in combination of two or more species. No particular limitation is imposed on the effective amount of calcium compound(s) for stabilizing α-thrombin, so long as stability of α-thrombin is increased. For example, the calcium concentration in the thrombin-containing solution is preferably 5 mM to 100 mM, more preferably 10 mM to 50 mM.

Specific examples of the organic acids include formic acid, acetic acid, propionic acid, butyric acid, valeric acid, oxalic acid, malonic acid, succinic acid, gluconic acid, lactic acid, glucuronic acid, glycolic acid, tartaric acid, malic acid, citric acid, glutaric acid, aminoacetic acid, and aminocaproic acid. These acids may be in the free acid form or the salt form. These organic acids may be used singly or in combination of two or more species.

No particular limitation is imposed on the amount(s) of organic acid(s) added to the thrombin-containing solution, so long as the stability of the α-thrombin-containing solution is increased. For example, the organic acid concentration in the thrombin-containing solution is preferably 10 mM to 500 mM, more preferably 50 mM to 200 mM.

Examples of the surfactants may be any of anionic surfactants, cationic surfactants, ampholytic surfactants, and non-ionic surfactants. Specifically, the surfactants include the following.

Examples of the anionic surfactants include sodium dodecyl sulfate, sodium dodecyl sulfonate, sodium dodecyl-N-sarcosinate, sodium cholate, sodium deoxycholate, and sodium taurodeoxycholate.

Examples of the cationic surfactants include cetyltrimethylammonium bromide, tetradecylammonium bromide, and dodecylpyridinium chloride.

Examples of the ampholytic surfactants include 3-[(3-cholamidepropyl)dimethylammonio]-1-propanesulfonic acid (CHAPS), 3-[(3-cholamidepropyl)dimethylammonio]-2-hydroxy-1-propanesulfonic acid (CHAPSO), palmitoyllysolecithin, doecyl-N-betaine, and dodecyl-β-alanine.

Examples of the nonionic surfactants include octyl glucoside, heptyl thioglucoside, decanoyl-N-methylglucamide, polyoxyethylene dodecyl ether, polyoxyethylene heptamethylhexyl ether, polyoxyethylene isooctylphenyl ether (TRITON (registered trademark) X series), polyoxyethylene nonylphenyl ether, polyoxyethylene fatty acid ester, sucrose fatty acid ester, and polyoxyethylene sorbitol ester (TWEEN (registered trademark) series).

Among these surfactants, nonionic surfactants are particularly preferred. These surfactants may be used singly or in combination of two or more species.

No particular limitation is imposed on the amount(s) of surfactant(s) added to the thrombin-containing solution, so long as the stability of α-thrombin-containing solution is increased. For example, the surfactant concentration in the α-thrombin-containing solution is preferably 0.001 to 1 w/v %, more preferably 0.005 to 0.1 w/v %.

Specific examples of the proteins include albumin, gelatin, and globulin. These proteins may be used singly or in combination of two or more species.

No particular limitation is imposed on the amount(s) of protein(s) added to the thrombin-containing solution, so long as the stability of α-thrombin-containing solution is increased. For example, the protein concentration in the α-thrombin-containing solution is preferably 0.05 to 10 w/v %, more preferably 0.1 to 5 w/v %.

The α-thrombin-containing solution of the present invention may further contain high-molecular-weight polysaccharides and/or synthetic polymers in order to enhance reproducibility of measurement, so long as fibrinogen assay is not impeded.

Specific examples of the high-molecular-weight polysaccharides include dextran 40, dextran 70, dextran 200,000, dextran 500,000, and Ficoll. These high-molecular-weight polysaccharides may be used singly or in combination of two or more species.

No particular limitation is imposed on the amount(s) of high-molecular-weight polysaccharide(s) added to the thrombin-containing solution, so long as the reproducibility of measurement is enhanced. For example, the high-molecular-weight polysaccharide concentration in the thrombin-containing solution is preferably 0.1 to 10 w/v %, more preferably 0.3 to 3 w/v %.

Specific examples of the synthetic polymers include polyvinyl alcohol 500, polyvinyl alcohol 1500, polyvinyl alcohol 2000, polyethylene glycol 1500, polyethylene glycol 2000, polyethylene glycol 4000, polyethylene glycol 6000, polyethylene glycol 8000, polyethylene glycol 20000, and polyvinylpyrrolidone. These synthetic polymers may be used singly or in combination of two or more species.

No particular limitation is imposed on the amount(s) of synthetic polymer(s) added to the thrombin-containing solution, so long as the reproducibility of measurement is enhanced. For example, the synthetic polymer concentration in the thrombin-containing solution is 0.1 to 10 w/v %, preferably 0.3 to 3 w/v %.

To the thrombin-containing solution of the present invention, appropriate preservatives may be added, so long as fibrinogen assay is not impeded. Examples of the preservatives include sodium azide, PROCLIN (registered trademark) 300, ciprofloxacin, propionic acid, and sodium benzoate. One or more preservatives selected therefrom may be used. If necessary, generally employed stabilizing agents such as salt (e.g., sodium chloride), amino acid, and saccharide may be added to the solution.

No particular limitation is imposed on the amount(s) of preservative(s) added to the thrombin-containing solution, so long as the amount(s) fall(s) within a predetermined range. For example, the PROCLIN (registered trademark) 300 concentration in the thrombin-containing solution is 0.001 to 1 w/v %, preferably 0.01 to 0.1 w/v %, which are the concentrations with respect to the commercial PROCLIN (registered trademark) 300 with a concentration of 100 w/v %.

The liquid fibrinogen assay reagent of the present invention contains the aforementioned α-thrombin-containing solution and may further contain compounds generally employed for fibrinogen assay so long as the fibrinogen assay is not impeded.

The liquid fibrinogen assay reagent may be employed as a clotting performance testing reagent, particularly a fibrinogen assay reagent. In a specific procedure, a fibrinogen standard solution is diluted, to a predetermined concentration, with a buffer for sample dilution, and the thus-diluted fibrinogen standard solution and the liquid fibrinogen assay reagent are mixed together. The clotting time is measured at 37° C. From the fibrinogen concentration and the clotting time measured, a calibration curve is obtained. A clotting time of an assay sample can be measured and converted by means of the calibration curve, to thereby obtain the fibrinogen concentration in the assay sample.

The liquid fibrinogen assay reagent of the present invention, containing a thrombin-containing solution, can be employed for determining activities of a substance inhibiting thrombin activity, e.g., anti-thrombin activity, hirudin activity, and chemical synthesis inhibitor activity.

The liquid fibrinogen assay reagent of the present invention may be provided as a kit including an assay reagent. In this case, the kit may further contain a sample dilution buffer for diluting a sample and a standard solution.

Examples of the sample dilution buffer include Good's buffer such as MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO and CAPS, and barbiturate buffer. These sample dilution buffers may be employed so that the pH of the thrombin-containing solution and the concentration as described above are adjusted to fall within the aforementioned ranges when the buffers are added to the thrombin-containing solution.

EXAMPLES

The present invention will next be described in detail by way of examples, which should not be construed as limiting the invention thereto.

Production Example 1

Separation/Purification of α-Thrombin and β/γ-Thrombin

A thrombin solution (50,000 units, prepared by dilution with 50 mM phosphate buffer (pH 7.0)), was adsorbed to S-Sepharose (2.5×11 cm, product of Pharmacia), washed with the same buffer, and eluted with the same buffer containing 0.4M NaCl with linear gradient (0 to 0.4M NaCl (each 300 mL)). The thrombin activity of the eluate was determined through the chromogenic substrate method to recover a β- and γ-thrombin mixture (hereinafter referred to as β/γ-thrombin) fraction, which was eluted at low ionic strength, and an α-thrombin fraction, which was eluted at high ionic strength.

Each thrombin solution fraction was adsorbed to Benzamidine-Sepharose (2.1×6 cm, product of Pharmacia), washed with the same buffer containing 0.5M NaCl, and eluted with the same buffer containing 0.1M benzamidine and 0.5M NaCl with linear gradient (0 to 0.1M benzamidine (each 100 mL)), to thereby recover purified α-thrombin (about 30,000 units) and purified β/γ-thrombin (about 10,000 units). Each of the thus-recovered purified thrombin solutions was dialyzed against 0.1M NaCl-20 mM Tris-HCl (pH 7.4) and employed in the subsequent studies. Thrombin activity was determined through the chromogenic substrate method. Specifically, each thrombin-containing solution (200 μL), which had been diluted to 500-fold with reagent 1 (100 mM Tris, 50 mM 3Na citrate, 0.05% BSA (pH 7.4)) was mixed with reagent 2 (S-2283: 1 mg/mL) (200 μL), and the mixture was allowed to react at 37° C. for 10 minutes. To the reaction mixture, 2% citric acid (1 mL) was added, and the absorbance was measured at 405 nm. The measurement obtained through the chromogenic substrate method was converted to thrombin activity based on the measurement from standard thrombin (Pharmacopoeia of Japan). As a result, the purified α-thrombin solution was found to have a concentration of 1,238 units/mL, and the purified β/γ-thrombin solution was found to have a concentration of 677 units/mL.

Production Example 2

Thrombin Purity Test (Densitometry)

Each of the purified α-thrombin and purified β/γ-thrombin was subjected to 10-20% SDS-polyacrylamide gel electrophoresis (SDS-PAGE) under non-reducing conditions through the Laemmli method. After protein staining with CBB, the gel was sufficiently destained. The coloring intensity of each band was measured by means of a densitometer (Kodak IS440CF).

As shown in Table 1 and FIG. 1, the purified α-thrombin was found to have a purity of about 95% (containing about 5% of β/γ-thrombin), and the purified β/γ-thrombin was found to have a purity of about 80% (containing about 20% of α-thrombin). In FIG. 1, A denotes a band attributed to α-thrombin, and B denotes a band attributed to β/γ-thrombin.

TABLE 1

|  | Intensity | | Relative content (%) | |
| --- | --- | --- | --- | --- |
|  | A | B | A | B |
| Purified α-thrombin | 74,040 | 4,195 | 94.6 | 5.4 |
| Purified β/γ-thrombin | 15,037 | 59,046 | 20.3 | 79.7 |

Example 1

Preparation of Thrombin-Containing Solutions Under Conditions 1 to 5

Each of the thrombin-containing solutions under conditions 1 to 5 was a solution (pH 6.3) prepared from 50 mM MES buffer containing α-thrombin (100 units/mL), 150 mM sodium chloride, 0.05% PROCLIN (registered trademark) 300, and β/γ-thrombin in an amount so as to attain the relative activity as below. The solutions were prepared from the purified α-thrombin and the purified β/γ-thrombin.

Condition 1: Relative β/γ-thrombin activity to total thrombin activity was 5%

Condition 2: Relative β/γ-thrombin activity to total thrombin activity was 10%

Condition 3: Relative β/γ-thrombin activity to total thrombin activity was 15%

Condition 4: Relative β/γ-thrombin activity to total thrombin activity was 20%

Condition 5: Relative β/γ-thrombin activity to total thrombin activity was 50%

Example 2

Stability in α-Thrombin Content

Each of the thrombin-containing solutions under conditions 1 to 5 was maintained at 37° C. for 0, 1, or 2 weeks, and the percent remaining of α-thrombin content was determined. The α-thrombin content was measured through the thrombin purity test as described in Production Example 2.

Figure 2:
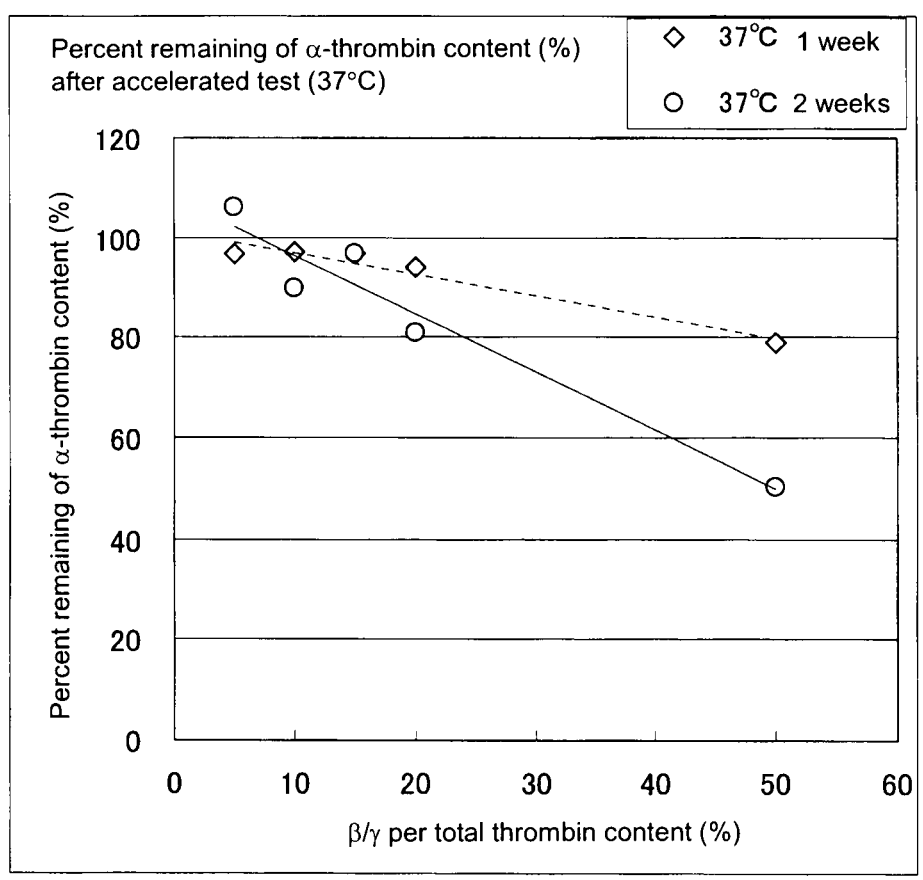
FIG. 2 A graph showing percentages of α-thrombin content remaining after an accelerated test (37° C.), with the clotting time on week 0 being 100%.

As shown in Table 2 and FIG. 2, the percent remaining of α-thrombin content after the accelerated test (37° C.) was found to decrease as the relative β/γ-thrombin activity increased. The thrombin-containing solution (condition 5) having a relative β/γ-thrombin activity of 50% exhibited a percent remaining of α-thrombin content of 50% after storage at 37° C. for two weeks, whereas the thrombin-containing solution (condition 4) having a relative β/γ-thrombin activity of 20% exhibited a percent remaining of α-thrombin content as high as 81% after storage at 37° C. for two weeks. Thus, the smaller the amount of co-present β/γ-thrombin (i.e., the higher the relative α-thrombin activity), the higher percentage of α-thrombin remained.

TABLE 2

Percent remaining of α-thrombin content after accelerated test

|  |  | Cond. 1 | Cond. 2 | Cond. 3 | Cond. 4 | Cond. 5 |
|---|---|---|---|---|---|---|
| (β/γ-Thrombin/total thrombin content) (%) |  | 5 | 10 | 15 | 20 | 50 |
|  | Storage period (37° C.) |  |  |  |  |  |
| Percent remaining of α-thrombin content (%) | 37° C., 0 day | 100.0 | 100.0 | 100.0 | 100.0 | 100.0 |
|  | 37° C., 1 week | 96.7 | 97.1 | 96.6 | 94.2 | 78.9 |
|  | 37° C., 2 weeks | 106.2 | 89.7 | 96.7 | 81.1 | 50.4 |

As shown in FIG. 2, the relative β/γ-thrombin activity to the total thrombin activity is inversely proportional to the percent remaining of α-thrombin content. Therefore, when the relative β/γ-thrombin activity is 30% (i.e., the relative α-thrombin activity to the total thrombin activity is 70%), the percent remaining of α-thrombin content after two-weeks' storage at 37° C. is estimated to 70% or higher. The result indicates that the α-thrombin content with respect to the total thrombin in a thrombin-containing solution is to be 70% or more, preferably 80% or more, more preferably 90% or more. The result also indicates that, still more preferably, the α-thrombin content is to be 70% or more and the β- and/or γ-thrombin content is to be less than 30% with respect to the amount of total thrombin in a thrombin-containing solution, yet more preferably, 80% or more and less than 20%, respectively, and particularly preferably, 90% or more and less than 10%, respectively.

Example 3

Stability in Thrombin Activity

In a manner similar to Example 1, each of the thrombin-containing solutions under conditions 1 to 5 was prepared and maintained at 37° C. for 0, 1, or 2 weeks, and the percent remaining of thrombin activity was determined from thrombin activity measured through the chromogenic substrate method.

The activity was determined through the chromogenic substrate method as described in Production Example 1.

Figure 3:
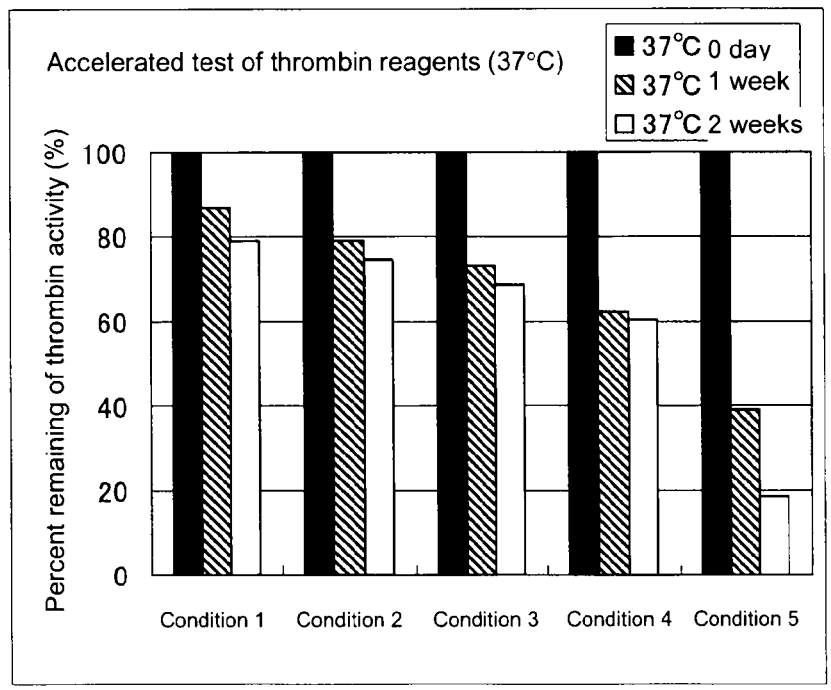
FIG. 3 A graph showing thrombin activity after an accelerated test (37° C.), with the clotting time on week 0 being 100%.

As shown in Table 3 and FIG. 3, the thrombin-containing solution (condition 5) having a relative β/γ-thrombin activity of 50% exhibited a percent remaining of thrombin activity of 20% or less after storage at 37° C. for two weeks, whereas the thrombin-containing solution (condition 4) having a relative β/γ-thrombin activity of 20% exhibited a percent remaining of thrombin activity as high as about 60% after storage at 37° C. for two weeks. Thus, the smaller the relative β/γ-thrombin activity (i.e., the higher the relative α-thrombin activity), the higher percentage of thrombin activity remained after storage at 37° C. for two weeks.

TABLE 3

Percent remaining of thrombin activity after accelerated test (37° C.)

|  |  | Cond. 1 | Cond. 2 | Cond. 3 | Cond. 4 | Cond. 5 |
|---|---|---|---|---|---|---|
| (β/γ-Thrombin/total thrombin content) (%) |  | 5 | 10 | 15 | 20 | 50 |
|  | Storage period (37° C.) |  |  |  |  |  |
| Percent remaining of α-thrombin content (%) | 37° C., 0 day | 100.0 | 100.0 | 100.0 | 100.0 | 100.0 |
|  | 37° C., 1 week | 86.8 | 79.2 | 73.4 | 62.1 | 39.2 |
|  | 37° C., 2 weeks | 79.2 | 74.4 | 68.8 | 60.2 | 18.6 |

Example 4

Stability in Clotting Activity of α-Thrombin-Containing Solutions

Each of the α-thrombin-containing solutions under conditions 1 to 5 which had been prepared in Example 2 and maintained at 37° C. for 0, 1, or 2 weeks was subjected to a clotting test using human plasma samples (sample 1 and sample 2). In the clotting test, a plasma sample was diluted to 10-fold with a sample diluting solution (TC buffer, product of Sysmex Corporation), and each thrombin-containing solution (50 μL) was added to the plasma solution (100 μL). The clotting time was measured by means of Coagrex 800 (product of Sysmex Corporation).

Figure 4:
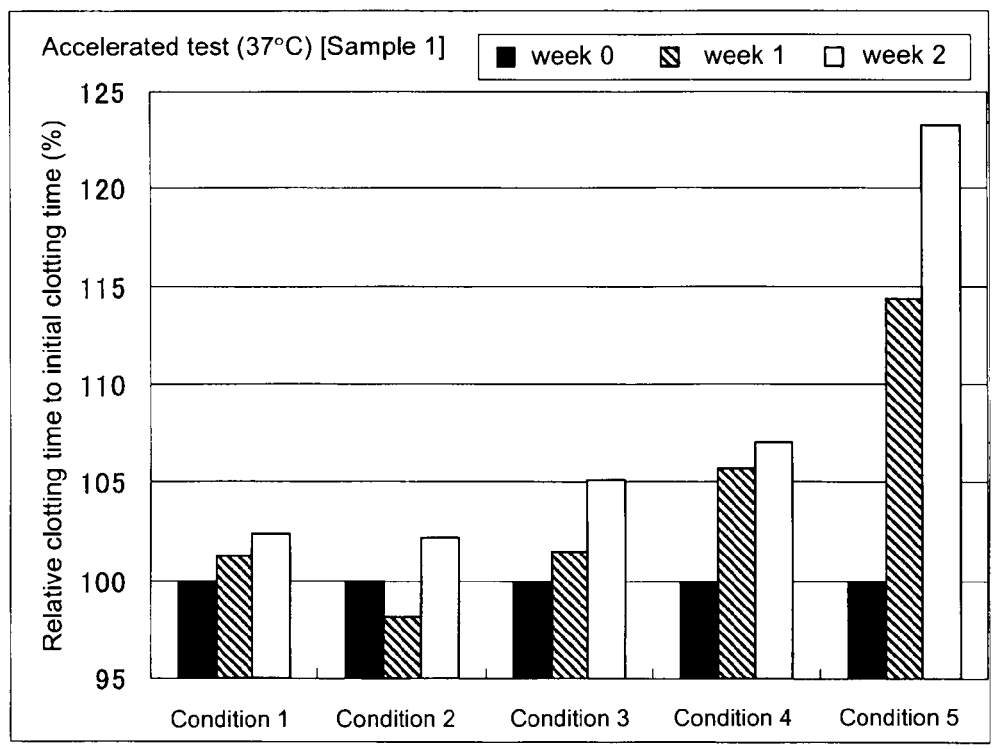
FIG. 4 A graph showing prolongation of clotting time observed in sample 1 after an accelerated test (37° C.), with the clotting time on week 0 being 100%.
Figure 5:
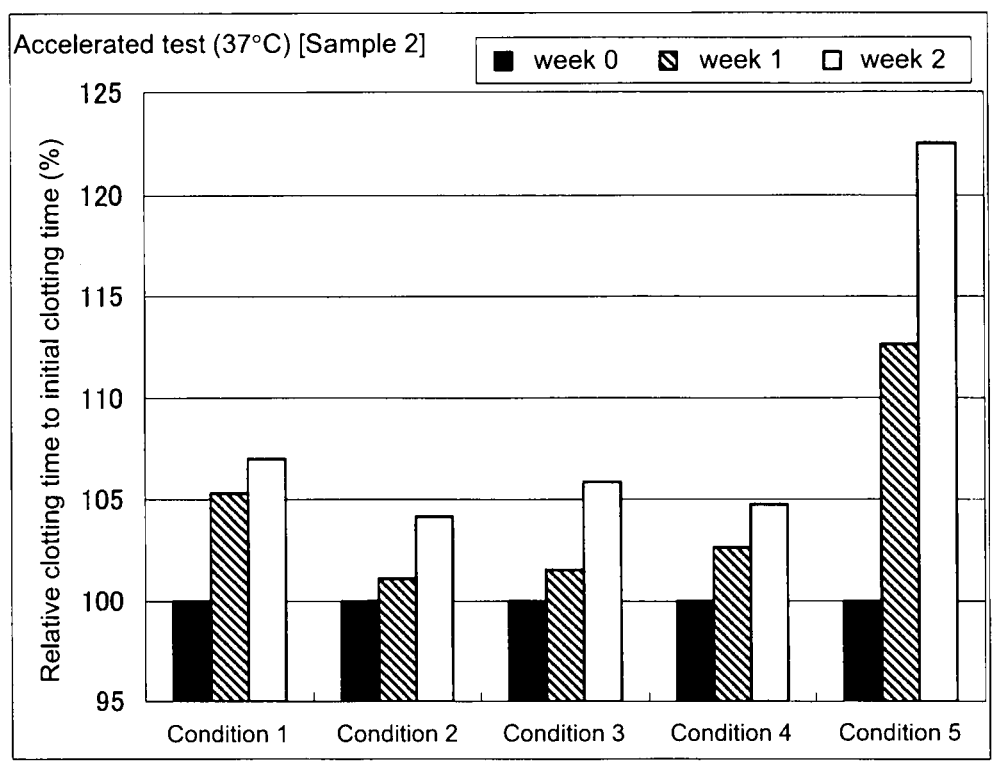
FIG. 5 A graph showing prolongation of clotting time observed in sample 2 after an accelerated test (37° C.), with the clotting time on week 0 being 100%.

The test results on sample 1 are shown in Table 4 and FIG. 4, and those on sample 2 are shown in Table 5 and FIG. 5. In FIGS. 4 and 5, the clotting time is represented by a relative time (%) with respect to a clotting time of 100% at week 0.

TABLE 4

Sample 1: Clotting time (sec) of sample 1 after accelerated test (37° C.)
(Sample 1: 290 mg/dL)

|  |  | Cond. 1 | Cond. 2 | Cond. 3 | Cond. 4 | Cond. 5 |
|---|---|---|---|---|---|---|
| ($\beta/\gamma$-Thrombin/total thrombin content) (%) |  | 5 | 10 | 15 | 20 | 50 |
|  | Storage period (37° C.) |  |  |  |  |  |
| Clotting time (sec) | 0 day | 13.6 | 13.8 | 13.7 | 14.5 | 14.6 |
|  | 1 week | 13.7 | 13.5 | 13.9 | 15.4 | 16.7 |
|  | 2 weeks | 13.9 | 14.1 | 14.4 | 15.6 | 18.0 |

TABLE 5

Sample 2: Clotting time (sec) of sample 2 after accelerated test (37° C.)
(Sample 2: 145 mg/dL)

|  |  | Cond. 1 | Cond. 2 | Cond. 3 | Cond. 4 | Cond. 5 |
|---|---|---|---|---|---|---|
| ($\beta/\gamma$-Thrombin/total thrombin content) (%) |  | 5 | 10 | 15 | 20 | 50 |
|  | Storage period (37° C.) |  |  |  |  |  |
| Clotting time (sec) | 0 day | 23.4 | 24.2 | 23.9 | 25.4 | 25.3 |
|  | 1 week | 24.6 | 24.4 | 24.3 | 26.0 | 28.5 |
|  | 2 weeks | 25.0 | 25.2 | 25.3 | 26.6 | 31.0 |

As shown in FIGS. 4 and 5, the thrombin-containing solution (condition 5) having a relative $\beta/\gamma$-thrombin activity of 50% exhibited a relative clotting time with respect to the initial clotting time of longer than 120% after storage at 37° C. for two weeks, whereas the thrombin-containing solutions (conditions 1 to 4) having a relative $\beta/\gamma$-thrombin activity of 20% or less exhibited a relative clotting time shorter than 110%. Therefore, the thrombin-containing solution of the present invention has been proven to be stable in solution and therefore, useful for a liquid fibrinogen assay reagent.

The invention claimed is:

1. A method for stabilizing $\alpha$-thrombin in a thrombin-containing solution, which comprises adjusting the percentage of $\alpha$-thrombin to 70% or more with respect to the amount of total thrombin in the thrombin-containing solution.

2. The method according to claim 1, wherein $\beta$- and/or $\gamma$-thrombin content with respect to the amount of total thrombin in the thrombin-containing solution is less than 30%.

3. The method according to claim 1 or 2, wherein the thrombin-containing solution has a pH of 4 to 9.

4. The method according to claim 1, wherein the thrombin concentration is 80% or more.

5. The method according to claim 1, wherein the thrombin concentration is 90% or more.

6. The method according to claim 3, wherein the thrombin-containing solution has a pH of 5.5 to 7.

7. The method according to claim 3, wherein the thrombin-containing solution has a pH of 6 to 6.5.

8. The method according to claim 1, wherein the $\alpha$-thrombin has an activity of 20 to 1,000 units/ml.

9. The method according to claim 1, wherein the $\alpha$-thrombin has an activity of 50 to 500 units/ml.

10. The method according to claim 1, wherein the $\alpha$-thrombin has an activity of 100 to 300 units/ml.

11. The method according to claim 1, wherein the thrombin-containing solution further comprises a calcium ion, an organic acid, a surfactant, and a protein.

12. The method of claim 1, wherein the thrombin-containing solution further comprises a calcium chloride, calcium lactate, calcium gluconate, calcium glucoronate, calcium tartrate, or a combination thereof.

13. The method according to claim 1, wherein the thrombin-containing solution further comprises formic acid, acetic acid, propionic acid, butyric acid, valeric acid, oxalic acid, malonic acid, succinic acid, gluconic acid, lactic acid, glucuronic acid, glycolic acid, tartaric acid, malic acid, citric acid, glutaric acid, aminoacetic acid, aminocaproic acid, or a combination thereof.

14. The method of claim 1, wherein the thrombin-containing solution further comprises albumin, gelatin, globulin or a combination thereof.

\* \* \* \* \*